US012337096B2

United States Patent
Furuhashi et al.

(10) Patent No.: US 12,337,096 B2
(45) Date of Patent: Jun. 24, 2025

(54) BLOOD PURIFICATION DEVICE

(71) Applicant: Nikkiso Company Limited, Tokyo (JP)

(72) Inventors: Tomohiro Furuhashi, Shizuoka (JP); Hideto Maki, Shizuoka (JP); Ferenc Kazinczi, Shizuoka (JP); Yuki Eda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 451 days.

(21) Appl. No.: 17/418,032

(22) PCT Filed: Aug. 29, 2019

(86) PCT No.: PCT/JP2019/033857
§ 371 (c)(1),
(2) Date: Jun. 24, 2021

(87) PCT Pub. No.: WO2020/137000
PCT Pub. Date: Jul. 2, 2020

(65) Prior Publication Data
US 2022/0088280 A1  Mar. 24, 2022

(30) Foreign Application Priority Data

Dec. 28, 2018 (JP) .................................. 2018-248125

(51) Int. Cl.
*A61M 1/36* (2006.01)
(52) U.S. Cl.
CPC .......... *A61M 1/369* (2013.01); *A61M 1/3623* (2022.05); *A61M 2205/3368* (2013.01)
(58) Field of Classification Search
None
See application file for complete search history.

(56) References Cited

U.S. PATENT DOCUMENTS 9,855,381 B2   1/2018  Tenyi et al.
10,300,191 B2  5/2019  Mochizuki et al.
(Continued)

FOREIGN PATENT DOCUMENTS

CN   107847655 A    3/2018
EP     3103495 A1  12/2016
(Continued)

OTHER PUBLICATIONS

Japanese Office Action for Application No. 2018-248125, dated May 31, 2022, with English translation, 10 pages.
(Continued)

*Primary Examiner* — Peter Keyworth
(74) *Attorney, Agent, or Firm* — Young Basile Hanlon & MacFarlane, P.C.

(57) ABSTRACT

A blood purification device includes a blood circuit for extracorporeally circulating blood of a patient; a liquid supply circuit for supplying a supply liquid to the blood circuit or to a blood purifier provided on the blood circuit and a warmer provided on the liquid supply circuit to warm the supply liquid. The warmer is configured to sandwich and hold a warming circuit constituting a part of the liquid supply circuit. The warmer includes a heater provided on a sandwiching-and-holding surface sandwiching and holding the warming circuit. The warmer includes a heater temperature detection unit capable of detecting temperature of the heater. The warmer includes a temperature sensor for liquid temperature detection being capable of detecting temperature of the supply liquid flowing through the warming circuit and being provided on the sandwiching-and-holding surface at a position at which the temperature sensor for liquid temperature detection is separated from the heater and, when sandwiching and holding the warming circuit, comes into contact with the warming circuit on the downstream side of
(Continued)

a portion warmed by the heater in a direction of sending liquid.

8 Claims, 5 Drawing Sheets

(56) References Cited

U.S. PATENT DOCUMENTS

| | | | |
|---|---|---|---|
| 11,351,291 B2* | 6/2022 | Kreymann | A61M 1/1609 |
| 2016/0361485 A1 | 12/2016 | Tenyi et al. | |
| 2018/0140766 A1 | 5/2018 | Mochizuki et al. | |

FOREIGN PATENT DOCUMENTS

| | | |
|---|---|---|
| JP | 2000-93449 A | 4/2000 |
| JP | 2002113096 A | 4/2002 |
| JP | 2017-730 A | 1/2017 |
| JP | 2017080266 A | 5/2017 |
| WO | 2017/014274 A1 | 1/2017 |

OTHER PUBLICATIONS

International Search Report for Application No. PCT/JP2019/033857, dated Nov. 19, 2019.
European Search Report for Application No. 19903507.2, dated Aug. 25, 2022, 14 pgs.
Chinese Office Action for Application No. 201980085953.3, dated Nov. 23, 2023, with English translation, 17 pgs.
Chinese Office Action for Application No. 201980085953.3, dated Aug. 1, 2024, with English translation, 12 pgs.
Chinese Office Action for Application No. 201980085953.3, dated May 14, 2024, with English translation, 13 pgs.

* cited by examiner

BLOOD PURIFICATION DEVICE

CROSS-REFERENCE TO RELATED APPLICATION(S)

This application is a national stage entry of International Application No. PCT/JP2019/033857, filed on Aug. 29, 2019, which claims priority to Japanese Application No. 2018-248125, filed on Dec. 28, 2018, the entire disclosures of which are hereby incorporated by reference.

TECHNICAL FIELD

The invention relates to a blood purification device.

BACKGROUND ART

When temperature of dialysate or replenishing liquid in blood purification device is low, it causes such a problem that temperature of blood returning to a patient is lowered and the patient feels cold. Thus, a blood purification device provided with a warmer for warming a supply liquid such as dialysate or replenishing liquid is used (see, e.g., Patent Document 1).

CITATION LIST

Patent Literature

Patent Document 1: JP 2017-080266A

SUMMARY OF INVENTION

Technical Problem

A blood purification device is known, in which a temperature sensor for liquid temperature detection (e.g., a clip-type temperature sensor, etc.) is provided separately from a warmer and the warmer is controlled so that the temperature of the supply liquid becomes a set temperature. However, with such a blood purification device, the temperature sensor for liquid temperature detection is forgotten to be attached or is not attached properly in some cases. In such cases, it may not be able to correctly control temperature of the supply liquid such as dialysate or replenishing liquid, hence, improvement is desired.

Therefore, it is an object of the invention to provide a blood purification device in which a problem in adjusting temperature of a supply liquid is less likely to occur.

Solution to Problem

The invention according to variation 1 is a blood purification device, comprising: a blood circuit for extracorporeally circulating blood of a patient; a liquid supply circuit for supplying a supply liquid to the blood circuit or to a blood purifier provided on the blood circuit; and a warmer provided on the liquid supply circuit to warm the supply liquid, wherein the warmer is configured to sandwich and hold a warming circuit as a part of the liquid supply circuit and comprises a heater provided on a sandwiching-and-holding surface sandwiching and holding the warming circuit, a heater temperature detection unit capable of detecting temperature of the heater, and a temperature sensor for liquid temperature detection being capable of detecting temperature of the supply liquid flowing through the warming circuit and being provided on the sandwiching-and-holding surface at a position at which the temperature sensor for liquid temperature detection is separated from the heater and, when sandwiching and holding the warming circuit, comes into contact with the warming circuit on the downstream side of a portion warmed by the heater in a direction of sending liquid.

The invention according to variation 2 is the blood purification device according to variation 1, comprising: a warmer attachment detection unit for detecting whether or not the warming circuit is attached to the warmer, based on the temperature of the heater detected by the heater temperature detection unit and the temperature of the supply liquid detected by the temperature sensor for liquid temperature detection.

The invention according to variation 3 is the blood purification device according to variation 2, wherein the warmer attachment detection unit determines that the warming circuit is not attached to the warmer when the temperature detected by the heater temperature detection unit reaches a predetermined upper limit temperature after the start of warming by the warmer and an increase in the temperature detected by the temperature sensor for liquid temperature detection from the start of warming by the warmer is less than a predetermined abnormality determination threshold.

The invention according to variation 4 is the blood purification device according to variation 1, comprising: a heater control unit for controlling the temperature of the heater so that the temperature of the supply liquid detected by the temperature sensor for liquid temperature detection becomes a set temperature that is preset, wherein the heater control unit is configured so as to be able to set an upper limit value of the temperature of the heater according to the supply liquid to be used.

The invention according to variation 5 is the blood purification device according to variation 4, wherein the heater control unit is configured so as to be able to change the upper limit temperature according to whether or not the supply liquid to be used contains a protein component.

The invention according to variation 6 is the blood purification device according to variation 5, wherein the upper limit temperature is less than 46 degrees when the supply liquid to be used contains a protein component, and the upper limit temperature is not less than 46 degrees when the supply liquid to be used does not contain any protein component.

The invention according to variation 7 is the blood purification device according to variation 1, wherein the heater temperature detection unit comprises a temperature sensor for heater provided in a warming region of the heater.

Advantageous Effects of Invention

According to the invention in variation 1, it is possible to provide a blood purification device in which a problem in adjusting temperature of a supply liquid is less likely to occur.

According to the invention in variation 2, it is possible to detect whether or not the warming circuit is attached to the warmer.

According to the invention in variation 3, it is possible to accurately detect whether or not the warming circuit is attached to the warmer.

According to the invention in variations 4 to 6, it is possible to suppress coagulation of protein component when a supply liquid containing a protein component is used.

According to the invention in variation 7, it is possible to easily realize the heater temperature detection unit at low cost.

DESCRIPTION OF EMBODIMENT

Embodiment

An embodiment of the invention will be described below in conjunction with the appended drawings.

Figure 1:
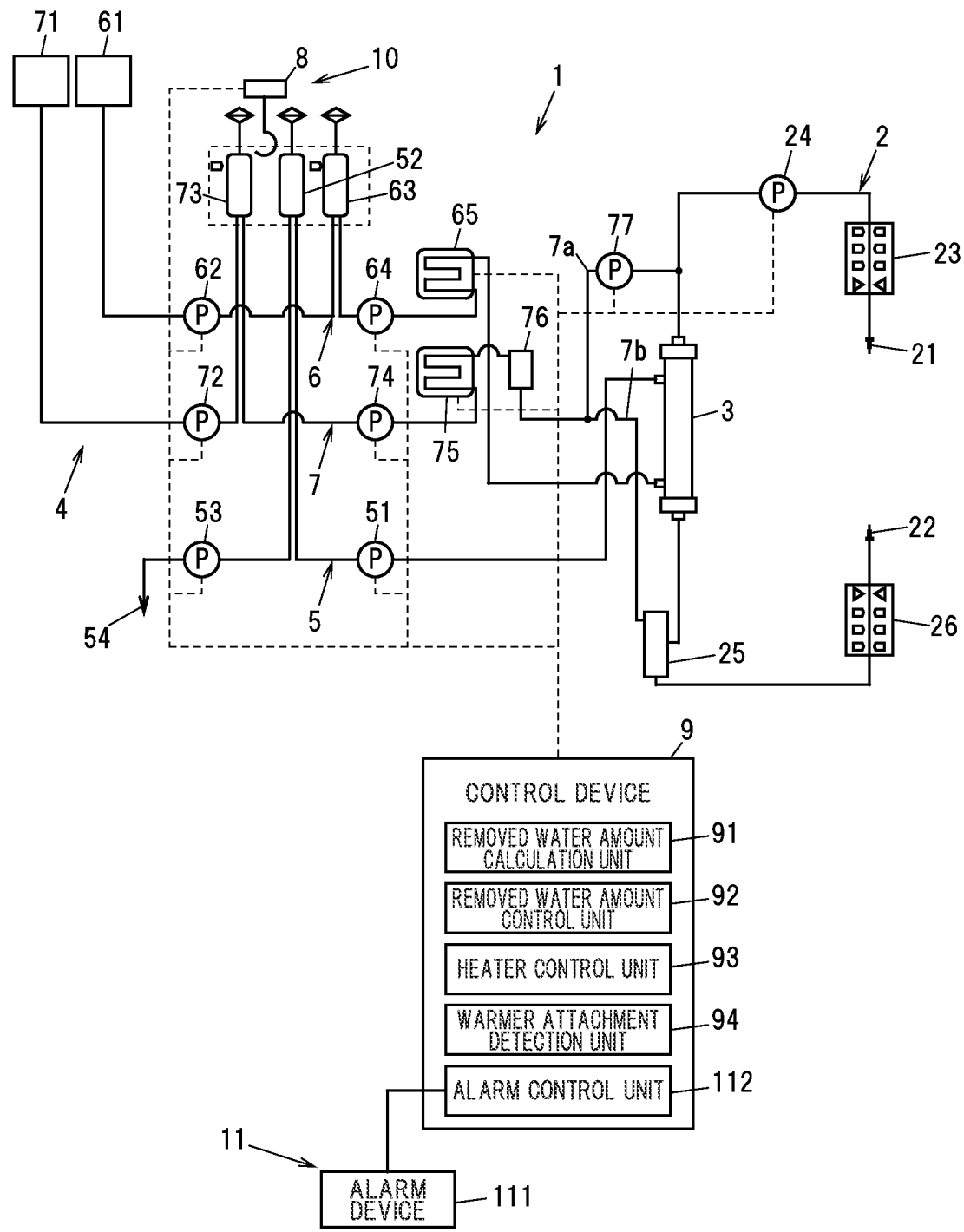
FIG. 1 is a schematic configuration diagram illustrating a blood purification device in an embodiment of the present invention.

FIG. 1 is a schematic configuration diagram illustrating a blood purification device in the present embodiment. As shown in FIG. 1, a blood purification device 1 includes a blood circuit 2 for extracorporeally circulating blood of a patient, a blood purifier 3 being provided on the blood circuit 2 and purifying the blood, liquid supply circuits 4 for supplying supply liquids to the blood purifier 3 or the blood circuit 2, and a waste liquid circuit 5 for discharging a waste liquid from the blood purifier 3. The blood circuit 2, the liquid supply circuits 4 (a dialysate circuit 6 and a replenishing liquid circuit 7 described later) and the waste liquid circuit 5 are composed of flexible tubes.

An artery-side puncture needle 21 is provided at one end of the blood circuit 2, and a vein-side puncture needle 22 is provided at the other end. In addition, a first air bubble detector 23, a blood pump 24, the blood purifier 3, a gas-liquid separator 25 and a second air bubble detector 26 are sequentially provided on the blood circuit 2 from the artery-side puncture needle 21-side toward the vein-side puncture needle 22-side. The first air bubble detector 23 and the second air bubble detector 26 each have an air bubble detection sensor for detecting air bubbles and a mechanism for clamping (gripping and blocking) the blood circuit 2 when air bubbles are detected.

The blood pump 24 is composed of a peristaltic pump that squeezes the tube to cause blood to flow toward the blood purifier 3. The blood purifier 3 is a device also called a dialyzer and purifies the blood by bringing the blood into contact with a dialysate through a blood purification membrane (not shown). The gas-liquid separator 25 is configured to remove air bubbles and allows passage of only liquid toward the vein-side puncture needle 22-side.

In the present embodiment, the blood purification device 1 has two circuits, the dialysate circuit 6 for supplying a dialysate and the replenishing liquid circuit 7 for supplying a replenishing liquid, as the liquid supply circuits 4 so as to be able to perform various treatments. In this regard, however, the blood purification device 1 may have only one of the dialysate circuit 6 and the replenishing liquid circuit 7.

A dialysate storage bag 61 holding the dialysate is connected to one end of the dialysate circuit 6. The other end of the dialysate circuit 6 is connected to a dialysate introduction port of the blood purifier 3. A dialysate transfer pump 62, a dialysate subdivision chamber 63 for temporarily storing the dialysate, a dialysate pump 64, and a dialysate warmer 65 are sequentially provided on the dialysate circuit 6 from the dialysate storage bag 61-side toward the blood purifier 3-side.

The dialysate transfer pump 62 and the dialysate pump 64 are each composed of a peristaltic pump that squeezes the tube to cause the dialysate to flow. The dialysate transfer pump 62 is used to transfer the dialysate in the dialysate storage bag 61 to the dialysate subdivision chamber 63. The dialysate pump 64 is used to cause the dialysate in the dialysate subdivision chamber 63 to flow toward the blood purifier 3. Having the dialysate subdivision chamber 63 allows the dialysate storage bag 61 to be replaced without interrupting the treatment. The dialysate warmer 65 is to warm the dialysate to an appropriate temperature so that the temperature of the blood to be returned to the patient is not lowered, and it is one aspect of the warmer of the invention. The details of the dialysate warmer 65 will be described later.

A replenishing liquid storage bag 71 holding the replenishing liquid is connected to one end of the replenishing liquid circuit 7. A replenishing liquid transfer pump 72, a replenishing liquid subdivision chamber 73 for temporarily storing the replenishing liquid, a replacement pump 74, a replenishing liquid warmer 75 and a gas-liquid separator 76 for replenishing liquid are sequentially provided on the replenishing liquid circuit 7 on the downstream side of the replenishing liquid storage bag 71.

In addition, the replenishing liquid circuit 7 branches off on the downstream side of the gas-liquid separator 76 for replenishing liquid, and an end of a pre-fluid replacement circuit 7a as one of the branches of the replenishing liquid circuit 7 is connected to the blood circuit 2 between the blood purifier 3 and the blood pump 24. A pre-fluid replacement pump 77 is provided on the pre-fluid replacement circuit 7a. An end of a post-fluid replacement circuit 7b as the other branch of the replenishing liquid circuit 7 is connected to the gas-liquid separator 25 on the blood circuit 2.

The replenishing liquid transfer pump 72, the replacement pump 74 and the pre-fluid replacement pump 77 are each composed of a peristaltic pump that squeezes the tube to cause the replenishing liquid to flow. The replenishing liquid transfer pump 72 is used to transfer the replenishing liquid in the replenishing liquid storage bag 71 to the replenishing liquid subdivision chamber 73. The replacement pump 74 is used to cause the replenishing liquid in the replenishing liquid subdivision chamber 73 to flow toward the blood circuit 2. The pre-fluid replacement pump 77 is activated when performing "pre-fluid replacement" to supply the replenishing liquid to the blood circuit 2 on the upstream side of the blood purifier 3. When the pre-fluid replacement pump 77 is not activated, the replenishing liquid pumped out by the replacement pump 74 passes through the post-fluid replacement circuit 7b, and "post-fluid replacement" for supplying the replenishing liquid to the blood circuit 2 on the downstream side of the blood purifier 3 (to the gas-liquid separator 25 in this example) is performed.

Having the replenishing liquid subdivision chamber 73 allows the replenishing liquid storage bag 71 to be replaced without interrupting the treatment. The replenishing liquid warmer 75 is to warm the replenishing liquid to an appropriate temperature so that the temperature of the blood to be returned to the patient is not lowered, and it is one aspect of the warmer of the invention. The gas-liquid separator 76 for replenishing liquid is to separate and remove air bubbles from the replenishing liquid.

One end of the waste liquid circuit 5 is connected to a waste liquid outlet of the blood purifier 3. A waste liquid pump 51, a waste liquid subdivision chamber 52 for temporarily storing the waste liquid and a discharge pump 53 are sequentially provided on the waste liquid line 5 on the downstream side of the blood purifier 3. The other end of the waste liquid line 5 is a waste liquid outlet 54 for discharging the waste liquid to the outside of the device.

The waste liquid pump 51 and the discharge pump 53 are each composed of a peristaltic pump that squeezes the tube to cause the waste liquid to flow. The waste liquid pump 51 is used to send the waste liquid to the waste liquid subdivision chamber 52. The discharge pump 53 is used to discharge the waste liquid in the waste liquid subdivision chamber 52 toward the waste liquid outlet 54.

The blood purification device 1 also has a removed water amount detection unit 10 that detects an amount of removed water based on a supplied amount of the supply liquid and a discharged amount of the waste liquid. The removed water amount detection unit 10 has the respective subdivision chambers 63, 73, 52, a load meter 8 as a weight detection mechanism capable of detecting a total weight of the respective subdivision chambers 63, 73, 52, and a removed water amount calculation unit 91.

The load meter 8 is configured to be able to detect a total weight of the dialysate subdivision chamber 63, the replenishing liquid subdivision chamber 73 and the waste liquid subdivision chamber 52. A detection value of the load meter 8 is output to a control device 9.

The removed water amount calculation unit 91 detects the amount of removed water by detecting a temporal change in the detection value of the load meter 8. The removed water amount calculation unit 91 is mounted on the control device 9 and is realized by appropriately combining an arithmetic element such as CPU, a memory, a storage device, a software, and an interface, etc.

The blood purification device 1 also includes a removed water amount control unit 92 that corrects a pump speed (a pump flow rate) of one or both of the liquid supply pump (the dialysate pump 64 and the replacement pump 74) and the waste liquid pump 51 so that the amount of removed water detected by the removed water amount detection unit 10 matches a target removed water amount. The removed water amount control unit 92 is mounted on the control device 9 and is realized by appropriately combining an arithmetic element such as CPU, a memory, a storage device, a software, and an interface, etc.

(Warmer and Control Thereof)

Now, the dialysate warmer 65 and control thereof will be described. Although the description of the replenishing liquid warmer 75 and control thereof will be omitted here, its structure is the same as that of the dialysate warmer 65 described below and the control thereof is performed in the same manner as the dialysate warmer 65.

Figure 2:
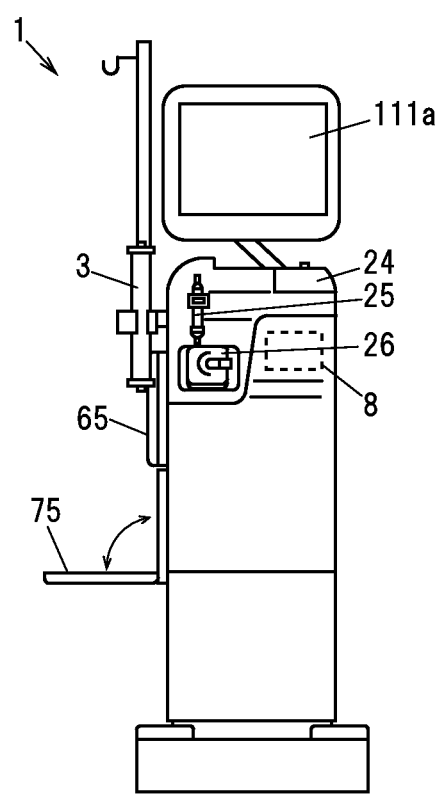
FIG. 2 is a diagram illustrating an outer appearance of the blood purification device of FIG. 1.
Figure 3:
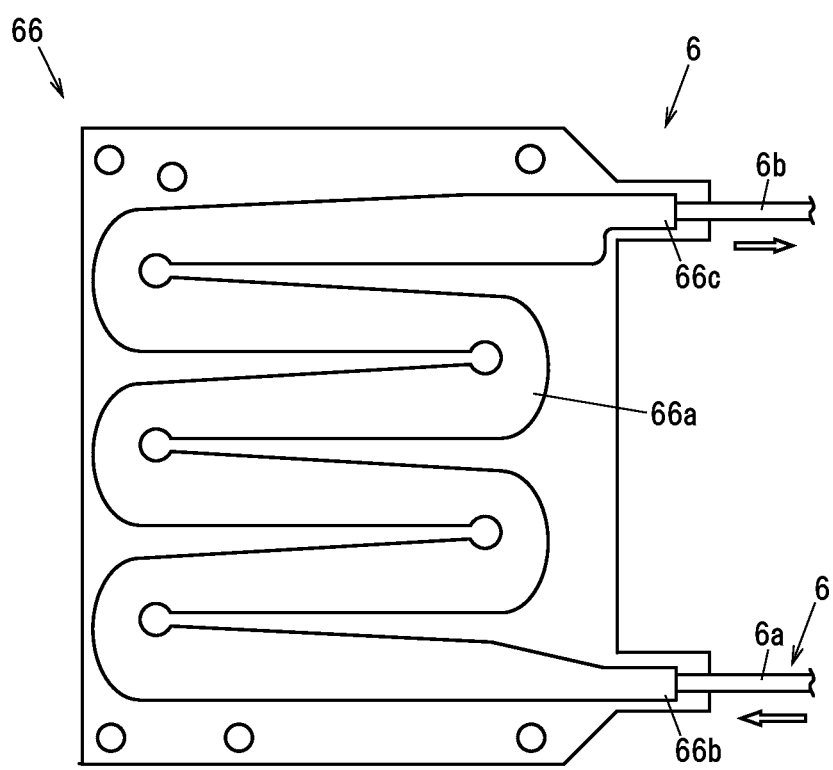
FIG. 3 is a plan view showing a warming circuit.
Figure 4A:
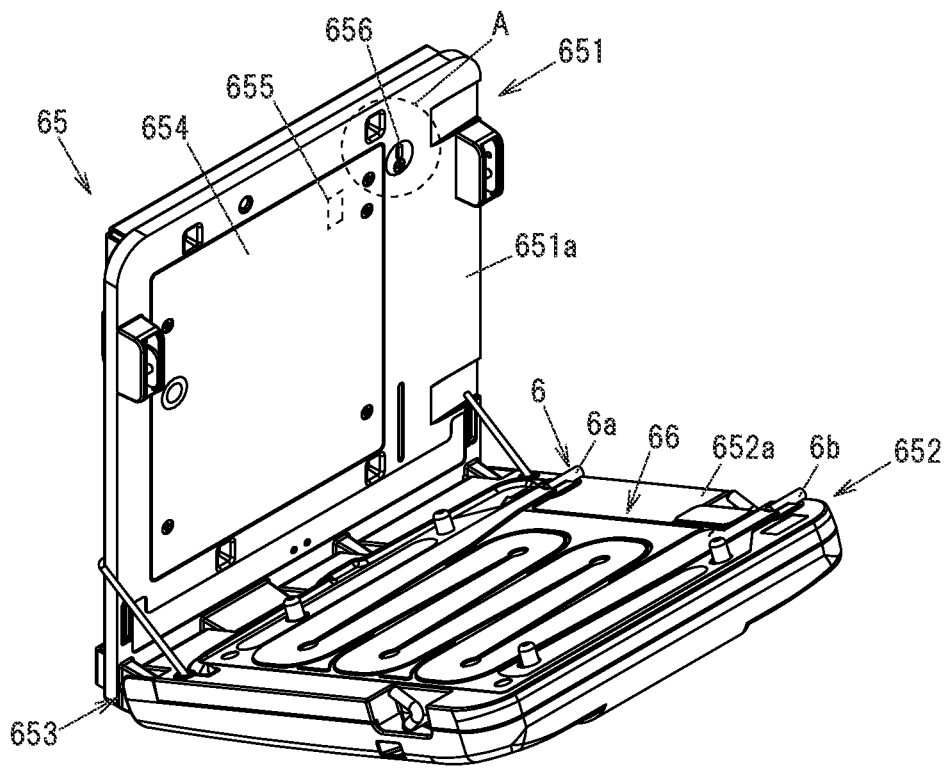
FIG. 4A is a perspective view showing a dialysate warmer.
Figure 4B:
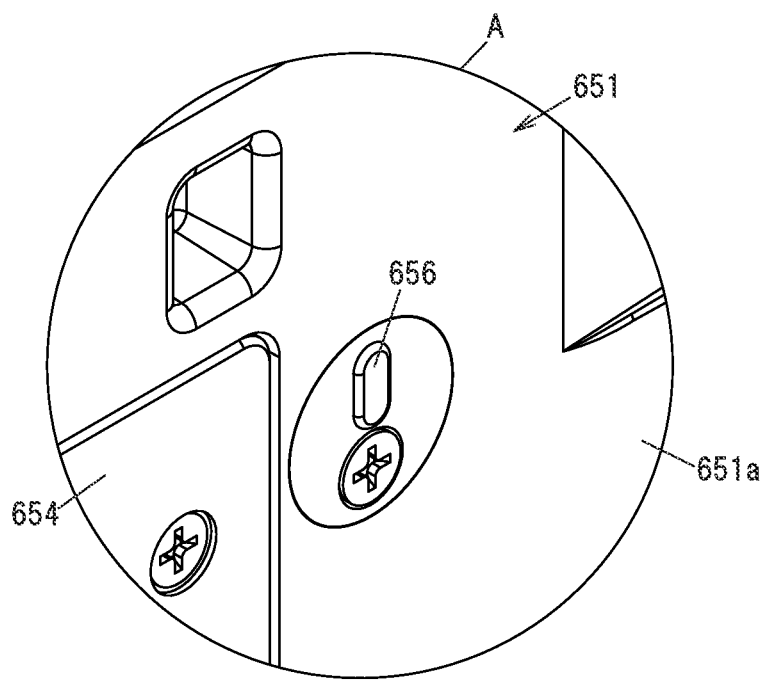
FIG. 4B is an enlarged view showing a portion A of FIG. 4A.

FIG. 2 is a diagram illustrating an outer appearance of the blood purification device 1. FIG. 3 is a plan view showing a warming circuit. FIG. 4A is a perspective view showing the dialysate warmer 65 and FIG. 4B is an enlarged view showing a portion A thereof. As shown in FIGS. 2, 3, 4A and 4B, the dialysate warmer 65 is provided on a side of the blood purification device 1 so as to be openable and closable.

The dialysate warmer 65 is configured to sandwich and hold a warming circuit 66 that is part of the dialysate circuit 6. As shown in FIG. 3, the warming circuit 66, also called a warming bag, has a flow route 66a formed by, e.g., stacking and fusing two flexible sheets. The flow route 66a is formed in a meandering manner. One end of the flow route 66a is a dialysate inlet port 66b and the other end is a dialysate outlet port 66c. A tube 6a extending from the dialysate pump 64 is connected to the inlet port 66b, and a tube 6b extending to the blood purifier 3 is connected to the outlet port 66c. The warming circuit 66 is made of a relatively soft material as compared to the tubes 6a, 6b. Therefore, the warming circuit 66, when being forgotten to be attached to the dialysate warmer 65 and left, not only causes the dialysate to be not warmed but also may get damaged for some reason or may causes the dialysate to be supplied to the blood purifier 3 at a flow rate different from an intended flow rate due to, e.g., the influence of external pressure or accumulation of the dialysate in the warming circuit 66. Therefore, when the warming circuit 66 is forgotten to be attached to the dialysate warmer 65, it is desired to notify the user of it.

The dialysate warmer 65 includes a fixed part 651 fixed to a side part of the blood purification device 1, and a lid part 652 pivotally provided on the fixed part 651 via a hinge part 653 provided at a lower part of the fixed part 651, and is configured that the warming circuit 66 is sandwiched and held between the fixed part 651 and the lid part 652. A plate-shaped heater 654 for warming the warming circuit 66 and thereby warming the dialysate flowing through the warming circuit 66 is provided on a sandwiching-and-holding surface 651a (a surface sandwiching and holding the warming circuit 66) of the fixed part 651. Although the heater 654 provided on the fixed part 651 will be described here, the heater 654 may be provided on the lid part 652 or may be provided on both of the fixed part 651 and the lid part 652.

The heaters 654 are provided to sandwich the flow route 66a (a meandering part) of the warming circuit 66 when the warming circuit 66 is sandwiched and held. Although the heaters 654 are provided on both the fixed part 651 and the lid part 652, the heater 654 may be provided on only one of them.

The dialysate warmer 65 also has a temperature sensor 655 for heater as a heater temperature detection unit capable of detecting temperature of the heater 654, and a temperature sensor 656 for liquid temperature detection capable of detecting temperature of the dialysate flowing through the warming circuit 66.

The temperature sensor 655 for heater is provided in a warming region of the heater 654 to detect the temperature of the heater 654, and is, e.g., a thermistor. The temperature sensor 655 for heater is mounted on the fixed part 651-side (on a side where the heater 654 is provided) in this example, but may be mounted on the lid part 652-side (on a side where the heater 654 is not provided). Alternatively, plural temperature sensors 655 for heater may be provided. In this regard, the heater temperature detection unit is not limited to the temperature sensor 655 for heater and may be configured using, e.g., a current sensor for detecting a current supplied to the heater 654. In this case, the temperature of the heater 654 is detected (estimated) based on a current value detected by the current sensor The temperature sensor 656 for liquid temperature detection is provided on the sandwiching-and-holding surface 651*a* at a position at which the temperature sensor 656 for liquid temperature detection is separated from the heater 654 and, when sandwiching and holding the warming circuit 66, comes into contact with the warming circuit 66 on the downstream side of a portion warmed by the heater 654 in a direction of sending liquid. That is, in the blood purification device 1, when the warming circuit 66 is attached to the dialysate warmer 65, the temperature sensor 656 for liquid temperature detection comes into contact with the warming circuit 66 without performing any other operation and is ready for detecting the temperature of the dialysate. Therefore, human errors such as forgetting to attach the sensor or its problematic attachment are less likely to occur, unlike when the temperature sensor 656 for liquid temperature detection is provided separately from the dialysate warmer 65. The temperature sensor 656 for liquid temperature detection is, e.g., a thermistor.

To suppress the influence of heat of the heater 654, the temperature sensor 656 for liquid temperature detection is desirably provided in a position shielded from heat of the heater 654 as much as possible. In the present embodiment, a member covering the periphery of the heater 654 (a member constituting the sandwiching-and-holding surface 651*a* around the heater 654) is made of a resin member having high heat insulating properties, and the temperature sensor 656 for liquid temperature detection is provided at a position separated from the heater 654 via such a member. The temperature sensor 656 for liquid temperature detection comes into contact with a surface of the warming circuit 66 and detects the temperature of the contact part. Since the warming circuit 66 is formed of thin sheets, the temperature of the surface of the warming circuit 66 is approximately equal to the temperature of the dialysate flowing through the warming circuit 66.

The blood purification device 1 includes a heater control unit 93 for controlling the temperature of the heater 654 so that the temperature of the dialysate detected by the temperature sensor 656 for liquid temperature detection becomes a set temperature that is preset. The heater control unit 93 sets, e.g., a target heater temperature based on a difference between the set temperature and the temperature of the dialysate, and performs temperature control of the heater 654 (control of the supply current, etc.) so that the temperature of the heater 654 detected by the temperature sensor 655 for heater becomes the target heater temperature. The heater control unit 93 is mounted on the control device 9 and is realized by appropriately combining an arithmetic element such as CPU, a memory, a storage device, a software, and an interface, etc.

The heater control unit 93 is preferably configured so as to be able to set an upper limit value of the temperature of the heater 654 (referred to as an upper limit temperature) according to the supply liquid (dialysate or replenishing liquid) to be used. Furthermore, the heater control unit 93 is preferably configured so as to be able to change the upper limit temperature according to whether or not the supply liquid to be used contains a protein component.

In particular, fresh frozen plasma containing protein components such as albumin is used as a supply liquid in a treatment mode called PE (plasma exchange therapy), PA (plasma adsorption), or DFPP (double filtration plasmapheresis). The protein components such as albumin have the property of coagulating into white solid when heated at a high temperature of not less than 46 degrees. The temperature at which coagulation of protein components occurs is different depending on the protein components and is about 41° C. to 46° C. Therefore, when the supply liquid to be used contains a protein component, the upper limit temperature should be less than 46° C., more preferably, not more than 40° C. On the other hand, for continuous hemodialysis (CHD), CHDF (continuous hemodiafiltration) or CHF (continuous hemofiltration), a dialysate not containing protein components is used and the upper limit temperature thus can be not less than 46 degrees.

Meanwhile, when warming, e.g., the supply liquid at a low temperature of less than 20° C., the temperature of the heater 654 may need to be raised to not less than 46° C. However, when the temperature is raised too much, there is a risk that a user gets burned when he/she touches a surface of the warmer 65 or 75 during tidying up, etc. Therefore, the temperature of the heater 654 is desirably controlled to a temperature with no risk of burn injury, e.g., less than 51° C. The heater control unit 93 is configured to stop warming by the heater 654 when, e.g., the temperature detected by the temperature sensor 655 for heater becomes not less than 51° C.

The temperature of the supply liquid at the time of joining the blood circuit 2 extracorporeally circulating the blood needs to be controlled to less than 46° C. This is because a phenomenon called hemolysis, which is the rupturing of red blood cells, occurs if the supply liquid at not less than 46° C. comes into contact with the blood. Therefore, it is necessary to monitor the detection value of the temperature sensor 656 for liquid temperature detection so that the temperature of the supply liquid at the time of joining the blood circuit 2 is less than 46° C. The heater control unit 93 is configured to stop warming by the heater 654 when, e.g., the temperature detected by the temperature sensor 656 for liquid temperature detection becomes not less than 46° C.

Since the temperature sensor 655 for heater acts to monitor overheating of the heater 654 while the temperature sensor 656 for liquid temperature detection acts to monitor overheating of the supply liquid as described above, the temperature sensor 655 for heater as the heater temperature detection unit and the temperature sensor 656 for liquid temperature detection are desirably provided independently.

The blood purification device 1 also includes a warmer attachment detection unit 94 for detecting whether or not the warming circuit 66 is attached to the warmer 65 or 75, based on the temperature of the heater 654 detected by the temperature sensor 655 for heater and the temperature of the dialysate detected by the temperature sensor 656 for liquid temperature detection. The warmer attachment detection unit 94 is mounted on the control device 9 and is realized by appropriately combining an arithmetic element such as CPU, a memory, a storage device, a software, and an interface, etc.

The warmer attachment detection unit 94 detects that the warming circuit 66 is not attached to the warmer 65 or 75 (i.e., the warming circuit 66 is forgotten to be attached) when the dialysate pump 64 is driven and the temperature of the dialysate does not increase even when the temperature of the heater 654 is increased.

Figure 5A:
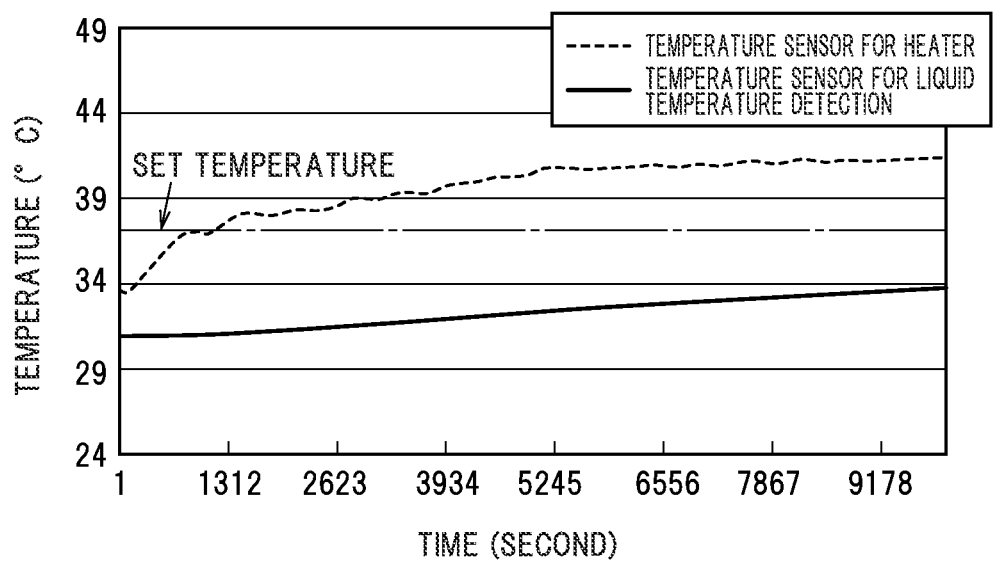
FIG. 5A is a graph showing changes in detection values of a temperature sensor for heater and a temperature sensor for liquid temperature detection in a state in which the warming circuit is not attached.

FIG. 5A is a graph showing changes in detection values of the temperature sensor 655 for heater and the temperature sensor 656 for liquid temperature detection in a state in which the warming circuit 66 is not attached. In this example, the dialysate flow rate is 1000 mL/h. As shown in FIG. 5A, in the state in which the warming circuit 66 is not attached, the detection value of the temperature sensor 656 for liquid temperature detection does not increase even when the heater temperature is increased, and the detection value of the temperature sensor 656 for liquid temperature detection does not reach the set temperature.

Figure 5B:
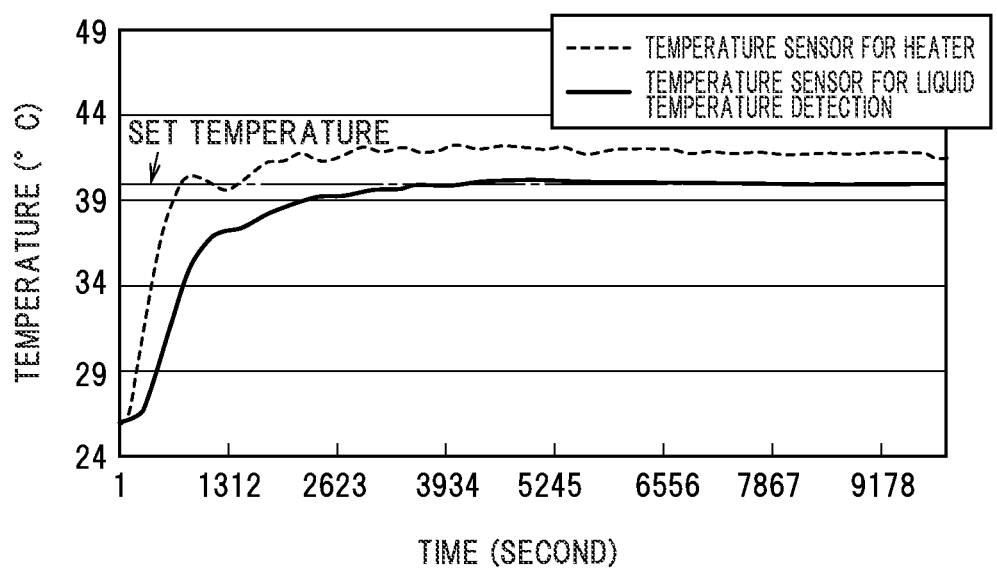
FIG. 5B is a graph showing changes in detection values of the temperature sensor for heater and the temperature sensor for liquid temperature detection in a state in which the warming circuit is attached.

FIG. 5B is a graph showing changes in detection values of the temperature sensor 655 for heater and the temperature sensor 656 for liquid temperature detection in a state in which the warming circuit 66 is attached. In this example, the dialysate flow rate is 1000 mL/h in the same manner as in FIG. 5A. As shown in FIG. 5B, in the state in which the warming circuit 66 is attached, the detection value of (the liquid temperature detected by) the temperature sensor 656 for liquid temperature detection increases with an increase in the heater temperature, and the detection value of the temperature sensor 656 for liquid temperature detection (the liquid temperature) reaches the set temperature. As such, the detection value of the temperature sensor 656 for liquid temperature detection changes significantly when the warming circuit 66 is attached and is not attached. Using such a change in the detection value of the temperature sensor 656 for liquid temperature detection due to whether or not the warming circuit 66 is attached, the warmer attachment detection unit 94 detects whether or not the warming circuit 66 is attached to the warmer 65 or 75.

In more particular, the warmer attachment detection unit 94 determines that the warming circuit 66 is not attached to the warmer 65 or 75 when the temperature detected by the temperature sensor 655 for heater reaches a predetermined upper limit temperature after the start of warming by the warmer 65 or 75 and an increase in the temperature detected by the temperature sensor 656 for liquid temperature detection from the start of warming by the warmer 65 or 75 is less than a predetermined abnormality determination threshold. That is, the warmer attachment detection unit 94 determines that the warming circuit 66 is not attached to the warmer 65 or 75 when the temperature detected by the temperature sensor 656 for liquid temperature detection does not increase sufficiently even though the temperature of the heater 654 is sufficiently increased. In this regard, a specific algorithm for determining that the warming circuit 66 is not attached to the warmer 65 or 75 is not limited thereto. For example, it may be configured such that, e.g., the temperature of the supply liquid at a position at which the temperature sensor 656 for liquid temperature detection is provided is estimated from the temperature of the supply liquid before warming, the temperature detected by the temperature sensor 655 for heater and the flow rate of the supply liquid, and it is determined that the warming circuit 66 is not attached to the warmer 65 or 75 when a difference between the estimated temperature and the temperature actually detected by the temperature sensor 656 for liquid temperature detection is greater than a predetermined threshold.

The blood purification device 1 further includes an alarm unit 11 that issues an alarm when the warmer attachment detection unit 94 detects that the warming circuit 66 is forgotten to be attached. The alarm unit 11 has an alarm device 111 that produces light, sound or vibration or displays a warning message on a display 111a such as monitor (see FIG. 2), and an alarm control unit 112 for controlling the alarm device 111. The alarm device 111 is composed of, e.g., a buzzer emitting a warning tone by sound and a display for displaying a warning message. The alarm control unit 112 causes, e.g., the buzzer to produce sound and the display to show a warning message. The alarm control unit 112 is mounted on the control device 9 and is realized by appropriately combining an arithmetic element such as CPU, a memory, a storage device, a software, and an interface, etc.

Functions and Effects of the Embodiment

As described above, in the blood purification device 1 in the present embodiment, the warmer 65 or 75 for warming the supply liquid is configured to sandwich and hold the warming circuit 66 as a part of the liquid supply circuit 4 and has the heater 654 provided on the sandwiching-and-holding surface 651a sandwiching and holding the warming circuit 66, the temperature sensor 655 for heater as the heater temperature detection unit capable of detecting the temperature of the heater 654, and the temperature sensor 656 for liquid temperature detection that is capable of detecting the temperature of the dialysate flowing through the warming circuit 66 and is provided on the sandwiching-and-holding surface 651a at a position at which the temperature sensor 656 for liquid temperature detection is separated from the heater 654 and, when sandwiching and holding the warming circuit 66, comes into contact with the warming circuit 66 on the downstream side of a portion warmed by the heater 654 in a direction of sending liquid.

By mounting both the heater temperature detection unit (the temperature sensor 655 for heater) and the temperature sensor 656 for liquid temperature detection on the warmer 65 or 75, it is possible to realize a blood purification device 1 which suppresses forgetting to attach the sensor or its problematic attachment and in which a problem in adjusting temperature of the supply liquid is less likely to occur. Use of both the sensors 655 and 656 also allows to detect that the warming circuit 66 is forgotten to be attached to the warmer 65 or 75. If the temperature sensor 656 for liquid temperature detection is provided separately from the warmer 65 or 75, it is not possible to judge whether the difference between the heater temperature and the liquid temperature is caused by forgetting to attach the warming circuit 66, or caused by forgetting to attach the temperature sensor 656 for liquid temperature detection or its problematic attachment. In addition, the temperature sensor 656 for liquid temperature detection, when being provided separately from the warmer 65 or 75, is affected by outside temperature between the warmer 65 or 75 and the attachment position of the temperature sensor 656 for liquid temperature detection, which causes an error in the liquid temperature control. However, in the present embodiment, the temperature sensor 656 for liquid temperature detection is less likely to be affected by the outside temperature by being provided on the warmer 65 or 75 and allows for liquid temperature adjustment (heater control) with higher accuracy according to the supply liquid to be used. In addition, by judging the presence or absence of the temperature sensor 656 for liquid temperature detection and the heater temperature detection unit which are essential for treatment in any case, it is not necessary to separately provide a sensor, etc., and the function of determining whether or not the warming circuit 66 is attached can be realized at low cost.

SUMMARY OF THE EMBODIMENT

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A blood purification device (1), comprising: a blood circuit (2) for extracorporeally circulating blood of a patient; a liquid supply circuit (4) for supplying a supply liquid to the blood circuit (2) or to a blood purifier (3) provided on the blood circuit (2); and a warmer (65, 75) provided on the liquid supply circuit to warm the supply liquid, wherein the warmer (65, 75) is configured to sandwich and hold a warming circuit (66) as a part of the liquid supply circuit (4)

and comprises a heater (654) provided on a sandwiching-and-holding surface (651*a*) sandwiching and holding the warming circuit (66), a heater temperature detection unit capable of detecting temperature of the heater (654), and a temperature sensor (656) for liquid temperature detection being capable of detecting temperature of the supply liquid flowing through the warming circuit (66) and being provided on the sandwiching-and-holding surface (651*a*) at a position at which the temperature sensor (656) for liquid temperature detection is separated from the heater (654) and, when sandwiching and holding the warming circuit (66), comes into contact with the warming circuit (66) on the downstream side of a portion warmed by the heater (654) in a direction of sending liquid.

[2] The blood purification device (1) described in [1], comprising: a warmer attachment detection unit (94) for detecting whether or not the warming circuit (66) is attached to the warmer (65, 75), based on the temperature of the heater (654) detected by the heater temperature detection unit and the temperature of the supply liquid detected by the temperature sensor (656) for liquid temperature detection.

[3] The blood purification device (1) described in [2], wherein the warmer attachment detection unit (94) determines that the warming circuit (66) is not attached to the warmer (65, 75) when the temperature detected by the heater temperature detection unit reaches a predetermined upper limit temperature after the start of warming by the warmer (65, 75) and an increase in the temperature detected by the temperature sensor (656) for liquid temperature detection from the start of warming by the warmer (65, 75) is less than a predetermined abnormality determination threshold.

[4] The blood purification device (1) described in any one of [1] to [3], comprising: a heater control unit (93) for controlling the temperature of the heater (654) so that the temperature of the supply liquid detected by the temperature sensor (656) for liquid temperature detection becomes a set temperature that is preset, wherein the heater control unit (93) is configured so as to be able to set an upper limit value of the temperature of the heater according to the supply liquid to be used.

[5] The blood purification device (1) described in [4], wherein the heater control unit (93) is configured so as to be able to change the upper limit temperature according to whether or not the supply liquid to be used contains a protein component.

[6] The blood purification device (1) described in [5], wherein the upper limit temperature is less than 46 degrees when the supply liquid to be used contains a protein component, and the upper limit temperature is not less than 46 degrees when the supply liquid to be used does not contain any protein component.

[7] The blood purification device (1) described in any one of [1] to [6], wherein the heater temperature detection unit comprises a temperature sensor (655) for heater provided in a warming region of the heater (654).

Although the embodiment of the invention has been described, the invention according to claims is not to be limited the embodiment described above. In addition, all combinations of the features described in the embodiment are not necessary to solve the problem of the invention. The invention can be appropriately modified and implemented without departing from the gist thereof.

REFERENCE SIGNS LIST

1: blood purification device
2: blood circuit
3: blood purifier
4: liquid supply circuit
5: waste liquid circuit
6: dialysate circuit
65: dialysate warmer (warmer)
654: heater
655: temperature sensor for heater
656: temperature sensor for liquid temperature detection
66: warming circuit
7: replenishing liquid circuit
75: replenishing liquid warmer (warmer)
9: control device
93: heater control unit
94: warmer attachment detection unit

The invention claimed is:

1. A blood purification device, comprising:
a blood circuit for extracorporeally circulating blood of a patient;
a liquid supply circuit for supplying a supply liquid to the blood circuit or to a blood purifier provided on the blood circuit; and
a warmer provided on the liquid supply circuit to warm the supply liquid, wherein the warmer is configured to sandwich and hold a warming circuit constituting a part of the liquid supply circuit and the warmer comprises:
a heater provided on a sandwiching-and-holding surface sandwiching and holding the warming circuit,
a housing portion that houses the warming circuit and a closing portion that covers the housing portion,
a heater temperature detection unit capable of detecting a temperature of the heater,
a temperature sensor for liquid temperature detection being capable of detecting a temperature of the supply liquid flowing through the warming circuit and being provided on the sandwiching-and-holding surface at a position at which the temperature sensor for liquid temperature detection is separated from the heater and, when sandwiching and holding the warming circuit, comes into contact with the warming circuit on a downstream side of a portion warmed by the heater in a direction of sending liquid, wherein the heater, the heater temperature detection unit, and the temperature sensor are all provided in the closing portion; and
a heater control unit that controls the temperature of the heater so that the temperature of the supply liquid detected by the temperature sensor for liquid temperature detection becomes a set temperature that is preset, wherein the heater control unit is configured to change an upper limit temperature according to a treatment mode performed by the blood purification device where the treatment mode is a plasma exchange therapy (PE), a plasma adsorption (PA), double filtration plasmapheresis (DFPP), continuous hemodialysis (CHD), continuous hemodiafiltration (CHDF), or continuous hemofiltration (CHF),
wherein in the plasma exchange therapy (PE), the plasma adsorption (PA), and double filtration plasmapheresis (DFPP), the supply liquid to be used contains protein components, wherein in the continuous hemodialysis (CHD), continuous hemodiafiltration (CHDF), and continuous hemofiltration (CHF), the supply liquid to be used does not contain protein components,
wherein the upper limit temperature is less than 46 degrees Celsius when the treatment mode is the plasma exchange therapy (PE), the plasma adsorption (PA), or double filtration plasmapheresis (DFPP) with protein components in the supply liquid to be used, wherein the upper limit temperature is not less than 46 degrees Celsius when the treatment mode is the continuous hemodialysis (CHD), continuous hemodiafiltration (CHDF), or continuous hemofiltration (CHF) without protein components in the supply liquid to be used;

wherein the closing portion has a thermal insulation member, the heater is arranged in the thermal insulation member, and the temperature sensor for liquid temperature detection is arranged away from the heater by the thermal insulation member; and wherein the temperature sensor for liquid temperature detection is provided spaced apart from the warming circuit so that the temperature sensor for liquid temperature detection and the warming circuit are free of contact when the warming circuit is not sandwiched by the heater, and the warming circuit contacts the temperature sensor for liquid temperature detection when the warming circuit is sandwiched by the heater.

2. The blood purification device according to claim 1, wherein the heater temperature detection unit comprises a temperature sensor for the heater provided in a warming region of the heater.

3. A blood purification device, comprising:

a blood circuit for extracorporeally circulating blood of a patient;

a liquid supply circuit for supplying a supply liquid to the blood circuit or to a blood purifier provided on the blood circuit;

a warmer provided on the liquid supply circuit to warm the supply liquid, wherein the warmer is configured to sandwich and hold a warming circuit constituting a part of the liquid supply circuit and comprises a heater provided on a sandwiching-and-holding surface sandwiching and holding the warming circuit, a heater temperature detection unit capable of detecting a temperature of the heater, and a temperature sensor for liquid temperature detection being capable of detecting temperature of the supply liquid flowing through the warming circuit and being provided on the sandwiching-and-holding surface at a position at which the temperature sensor for liquid temperature detection is separated from the heater and, when sandwiching and holding the warming circuit, comes into contact with the warming circuit on a downstream side of a portion warmed by the heater in a direction of sending liquid; and a warmer attachment detection unit for detecting whether or not the warming circuit is attached to the warmer, based on a temperature of the heater detected by the heater temperature detection unit and a temperature of the supply liquid detected by the temperature sensor for liquid temperature detection.

4. The blood purification device according to claim 3, wherein the warmer attachment detection unit determines that the warming circuit is not attached to the warmer when the temperature detected by the heater temperature detection unit reaches a predetermined upper limit temperature after a start of warming by the warmer and an increase in the temperature detected by the temperature sensor for liquid temperature detection from the start of warming by the warmer is less than a predetermined abnormality determination threshold.

5. The blood purification device according to claim 3, comprising:

a heater control unit for controlling the temperature of the heater so that the temperature of the supply liquid detected by the temperature sensor for liquid temperature detection becomes a set temperature that is preset, wherein the heater control unit is configured so as to be able to set an upper limit value of the temperature of the heater according to the supply liquid to be used.

6. The blood purification device according to claim 5, wherein the heater control unit is configured so as to be able to change an upper limit temperature according to whether or not the supply liquid to be used contains a protein component.

7. The blood purification device according to claim 6, wherein the upper limit temperature is less than 46 degrees when the supply liquid to be used contains a protein component, and the upper limit temperature is not less than 46 degrees when the supply liquid to be used does not contain any protein component.

8. The blood purification device according to claim 3, wherein the heater temperature detection unit comprises a temperature sensor for the heater provided in a warming region of the heater.

* * * * *